(12) United States Patent
Adachi et al.

(10) Patent No.: US 9,936,931 B2
(45) Date of Patent: Apr. 10, 2018

(54) BONE DENSITY MEASURING DEVICE

(71) Applicant: HITACHI ALOKA MEDICAL, LTD., Mitaka-shi, Tokyo (JP)

(72) Inventors: Ryutaro Adachi, Mitaka (JP); Yasuo Nakamura, Tokyo (JP); Naoto Kato, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 86 days.

(21) Appl. No.: 15/023,824

(22) PCT Filed: Sep. 18, 2014

(86) PCT No.: PCT/JP2014/074651
§ 371 (c)(1),
(2) Date: Mar. 22, 2016

(87) PCT Pub. No.: WO2015/046003
PCT Pub. Date: Apr. 2, 2015

(65) Prior Publication Data
US 2016/0242722 A1    Aug. 25, 2016

(30) Foreign Application Priority Data
Sep. 26, 2013   (JP) ................. 2013-200326

(51) Int. Cl.
*A61B 6/00*   (2006.01)
*A61B 6/04*   (2006.01)

(52) U.S. Cl.
CPC .............. *A61B 6/5217* (2013.01); *A61B 6/04* (2013.01); *A61B 6/0407* (2013.01);
(Continued)

(58) Field of Classification Search
None
See application file for complete search history.

(56) References Cited

U.S. PATENT DOCUMENTS 5,602,935 A * 2/1997 Yoshida ................. A61B 6/505
                                                          382/132
6,058,157 A    5/2000 Christiansen et al.
(Continued)

FOREIGN PATENT DOCUMENTS

JP       7-236630 A     9/1995
JP    2000-510723 A     8/2000
(Continued)

OTHER PUBLICATIONS

Notification of Transmittal of Translation of the International Preliminary Report on Patentability (Form PCT/IB/338) of International Application No. PCT/JP2014/074651 dated Mar. 31, 2016 with Form PCT/IPEA/409. (4 pages).
(Continued)

*Primary Examiner* — Hoon Song
(74) *Attorney, Agent, or Firm* — Westerman, Hattori, Daniels & Adrian, LLP (57) ABSTRACT

In image data obtained, the radius and the ulna, and interosseous soft tissue between two bones are identified. A midpoint (Ygk) of the length of the interosseous soft tissue in a Y axis direction in (Xk) coordinates is determined. This midpoint is determined in multiple coordinates, and an approximate straight line of these midpoints is determined and set as a reference line. The foot of the perpendicular from the ulna styloid process to the reference line is set as a reference position. A region of interest is set in a position at a predetermined distance from the reference position along the reference line.

6 Claims, 9 Drawing Sheets

(52) U.S. Cl.
CPC .......... *A61B 6/4405* (2013.01); *A61B 6/4435* (2013.01); *A61B 6/505* (2013.01); *A61B 6/54* (2013.01)

(56) References Cited

U.S. PATENT DOCUMENTS 6,430,427 B1    8/2002   Lee et al.
6,763,257 B1    7/2004   Rosholm et al.

FOREIGN PATENT DOCUMENTS

| JP | 2000-245722 A | 9/2000 |
|---|---|---|
| JP | 2000-300547 A | 10/2000 |
| JP | 2004-16392 A | 1/2004 |
| JP | 2009-100943 A | 5/2009 |
| JP | 4773295 B2 | 9/2011 |
| JP | 4829198 B2 | 12/2011 |

OTHER PUBLICATIONS

International Search Report dated Jan. 6, 2015, issued in counterpart International Application No. PCT/JP2014/074651 (2 pages).

\* cited by examiner

BONE DENSITY MEASURING DEVICE

TECHNICAL FIELD

The present invention relates to a bone density measuring device, and more particularly to a device suitable for Measuring bone density of the forearm.

BACKGROUND ART

Measurement of bone density (measurement of density of minerals of bones) provides significant data for diagnosis of osteoporosis and a follow-up treatment of osteoporosis, and various types of bone density measuring devices have been suggested. Bone density is measured by a variety of methods, including a method using radiation such as an X-ray, a method using an ultrasound wave, and other methods.

Bone density measuring devices that measure the bone density of the calcaneus, the radius, the second metacarpal bone, a lumbar vertebra, the femur, and the like using X-ray are known. If the radius is a target of measurement, for actual measurement, a predetermined region of the forearm placed and fixed on a table is irradiated with an X-ray from under the table, and the X-ray transmitting through the forearm is detected by a detector disposed within an arm portion of the device above the table for obtaining data. For a normal diagnosis, a region of interest is set using the position of an ulna styloid process as a reference. The region of interest is set in a position at a distance of 1/N (N is a natural number), more specifically, 1/10, 1/5, 1/3, for example, of a forearm length from the position of the ulna styloid process.

The bone density measuring devices for the forearm are disclosed in the following Patent Documents 1 and 2.

CITATION LIST

Patent Literature

[Patent Document 1] JP 4773295 B
[Patent Document 2] JP 4829198 B2

SUMMARY OF THE INVENTION

Technical Problem

The inclination of the forearm placed on the table (rotation of the forearm within a plane defined by the table) may affect the position and inclination of the region of interest. In particular, when measurements are performed at certain intervals, inconsistencies of the inclinations of the forearm may cause inconsistencies of the regions of interest, leading to a failure of comparison between the measurement results with sufficient accuracy.

It is therefore an advantage of the invention to reduce the effect of the inclination of the forearm place on the table on the measurement.

Solution to Problem

A bone density measuring device according to the invention includes an image data capturing unit configured to capture an image including the ulna and the radius, a tissue discrimination unit configured to discriminate between an image portion corresponding to a bone and an image portion corresponding to a soft tissue within image data which are captured, a reference line setting unit configured to set a reference line along a direction in which an interosseous soft tissue between the ulna and the radius extends, a reference position obtaining unit configured to obtain a reference position which is used as a reference for a measurement position a region of interest setting unit configured to set at least one region of interest at a position a predetermined distance from the reference position in a direction along the reference line, and a bone density calculation unit configured to calculate bone density within the region of interest which is set.

The reference line described above is determined based on a geometrical shape of the forearm, and is substantially fixed to the forearm. Setting the region of interest based on this reference line can reduce the effects caused by the inclination of the forearm.

The region of interest which is to be set can have a predetermined shape which is determined with reference to the reference line, and can have a shape of a rectangle having a pair of opposite sides which are parallel to the reference line.

The reference line setting unit obtains, in each of a plurality of positions on one coordinate axis of the image data which are captured, a midpoint of a length of the interosseous soft tissue in a direction orthogonal to the coordinate axis, and sets the reference line based on a plurality of midpoints which are obtained. An approximate straight line of the plurality of midpoints can be set as the reference line, for example.

The bone density measuring device may further include an ulna styloid process specification unit configured to specify an ulna styloid process using the image portion corresponding to a bone which is discriminated, and the reference position obtaining unit can obtain the reference position based on a position of the ulna styloid process. For example, the ulna styloid process specification unit determines an image portion corresponding to a bone on one side of the reference line as the ulna and specifies an end of this ulna in the longitudinal direction as the ulna styloid process. Further, the reference position obtaining unit sets the position of a foot of a perpendicular from the ulna styloid process to the reference line as a reference position, for example.

Advantageous Effects of Invention

Setting the region of interest based on the reference line which substantially fixed to the forearm enhances the reproducibility in setting the region of interest.

DESCRIPTION OF EMBODIMENTS

Figure 1:
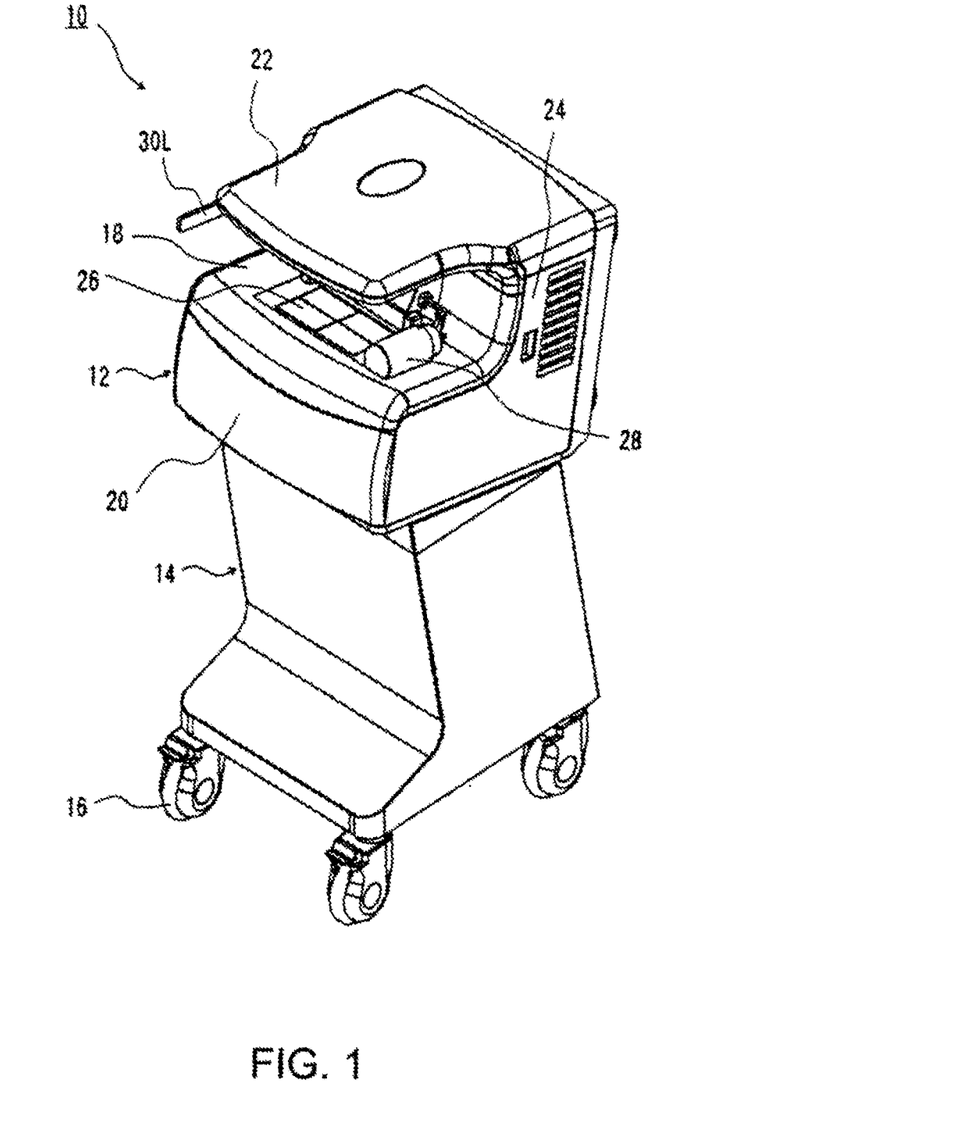
FIG. 1 is a perspective view illustrating an outer appearance of the bone density measuring device according to a present embodiment.

A preferred embodiment of the invention will be described with reference to the drawings. FIG. 1 is a perspective view illustrating an outer appearance of a bone density measuring device 10 according to an embodiment of the prevention. The bone density measuring device 10 includes a main body 12 storing equipment for measuring the bone density, and a leg portion 14 for supporting the main body 12 placed thereon at a predetermined height position and at a predetermined inclined angle, which is, in the present embodiment, 10°. The leg portion 14 has casters 16 with a stop function fixed thereto for facilitating movement and fixation of the device.

The main body 12 includes a base portion 20 having a table 18 on an upper surface thereof, on which the forearm is to be placed, an arm portion 22 disposed above the base portion 20 such that the forearm is positioned between the base portion 20 and the portion 22, and a wall portion 24 which stands upright from the base portion 20 so as to support the arm portion 22. The table 18 includes a top board 26 formed of a material through which an X-ray is transmissible, disposed substantially in the center of the table 18. In the very vicinity of the top board 26, there is positioned a grip 28 which is to be held by an examinee's hand of the forearm to be examined during measurement. An elbow rest 30L which comes into contact with the elbow of the forearm is further supported on an elbow rest support rod 34L extending from a rod support portion 32 fixed to the base portion 20 (see FIG. 2). While the grip 28 is positioned on the right side of the top board 26 in the drawing of FIG. 1, the grip 28 may be positioned on the left side, in which case, an elbow rest 30R is disposed on the right side (see FIG. 2).

Figure 2:
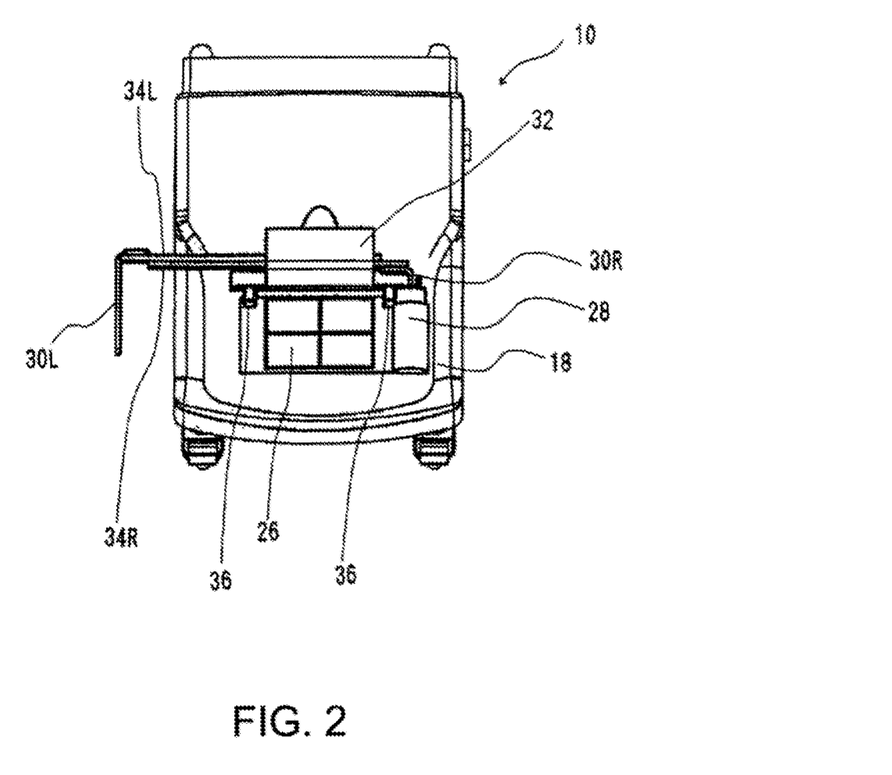
FIG. 2 is a plan view of the hone density measuring device according to the present embodiment, in which an arm portion is partially omitted.

FIG. 2 is a plan view in which the arm portion 22 is partially omitted so as to make the structure on the table 18 visible. On the right and left sides of the rod support portion 32, there are disposed contact pads 36 which come into contact with the forearm for positioning the forearm toward the depth direction. FIG. 2 shows, in addition to the elbow rest 30L shown on the left side of the main body 12 in the drawing of FIG. 1 and the elbow rest support rod 34L, the elbow rest 30R and an elbow rest support rod 34R, which supports the elbow rest 30R. The rod support portion 32 stores therein an encoder or a potentiometer for detecting the amount of movement of the support rods 34L and 34R. The position of the grip 28 can be changed and the two elbow rests and the two elbow rest support rods are provided, such that both of the right and left forearms can be measured. More specifically, if the position of the grip 28 is changed from the right side of the rod support portion 32 as shown to the left side thereof, measurement for the right forearm can be performed.

Figure 3:
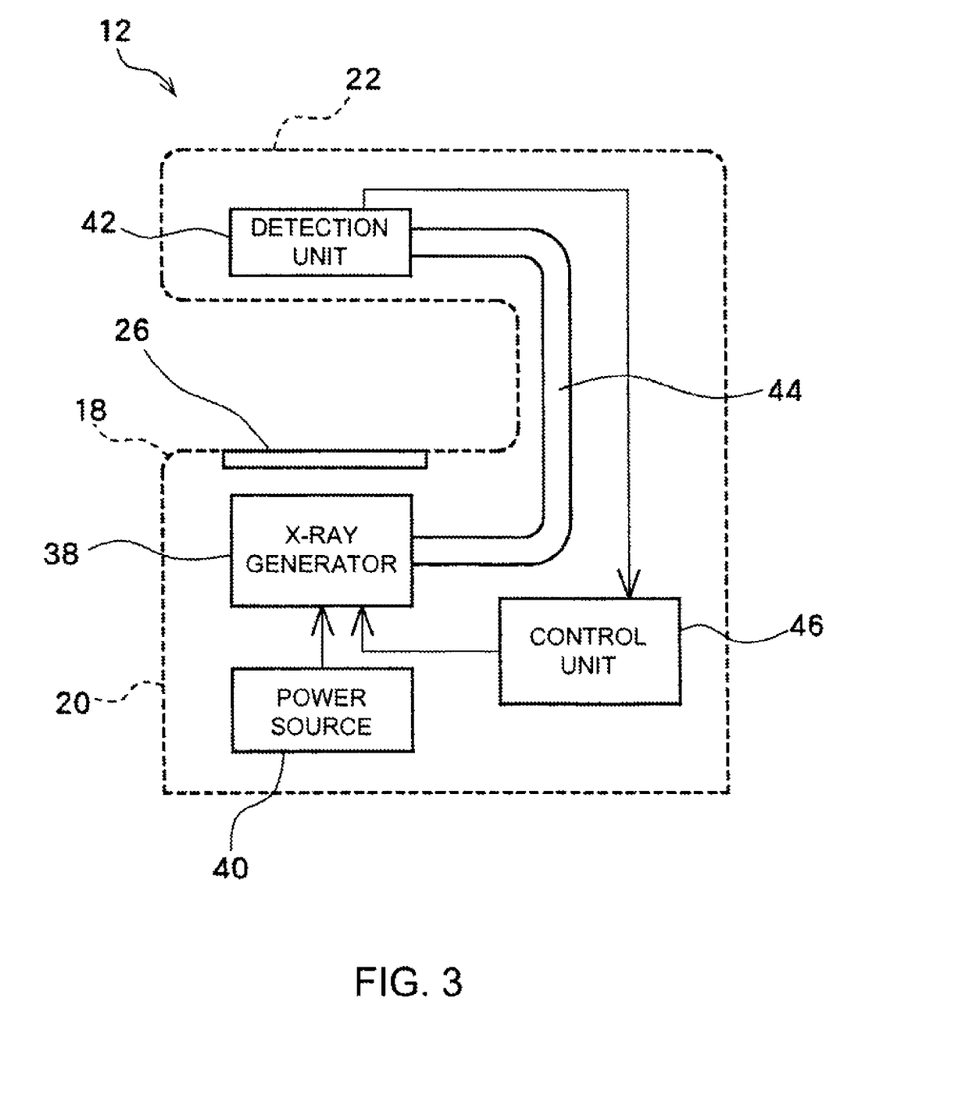
FIG. 3 is a block diagram illustrating a structure related to capturing of an X-ray image of the bone density measuring device according to the present embodiment.

FIG. 3 is a block diagram illustrating an internal structure of the main body 12, particularly a structure related to measurement using an X-ray. The base portion 20 of the main body 12 stores therein an X-ray generator 38 and a power source 40 for supplying power to the X-ray generator 38. The X-ray generator 38 emits X-rays in a fan beam shape, and the X-rays which are emitted are detected by a detection unit 42 stored in the arm portion 22. The detection unit 42 includes a one-dimensional array of detection elements corresponding to the fan beam shape. The X-ray generator 38 and the detection unit 42 are coupled with each other through a bracket 44, and move within the main body 12 in a coupled state in the right and left direction in FIG. 2. The beam shape of the X-ray is not limited to a fan beam, and may be a pencil beam or a cone beam. The direction in which the X-ray generator 38 is movable is determined in accordance with the beam shape.

Moving the X-ray generator 38 and the detection unit 42 in the right and left direction with the X-ray generator 38 emitting an X-ray having a fan beam shape and the detection unit 42 detecting the emitted X-ray enables collection two-dimensional X-ray data. These data are then captured a control unit 46, which then executes predetermined processing to calculate the bone density.

Figure 4:
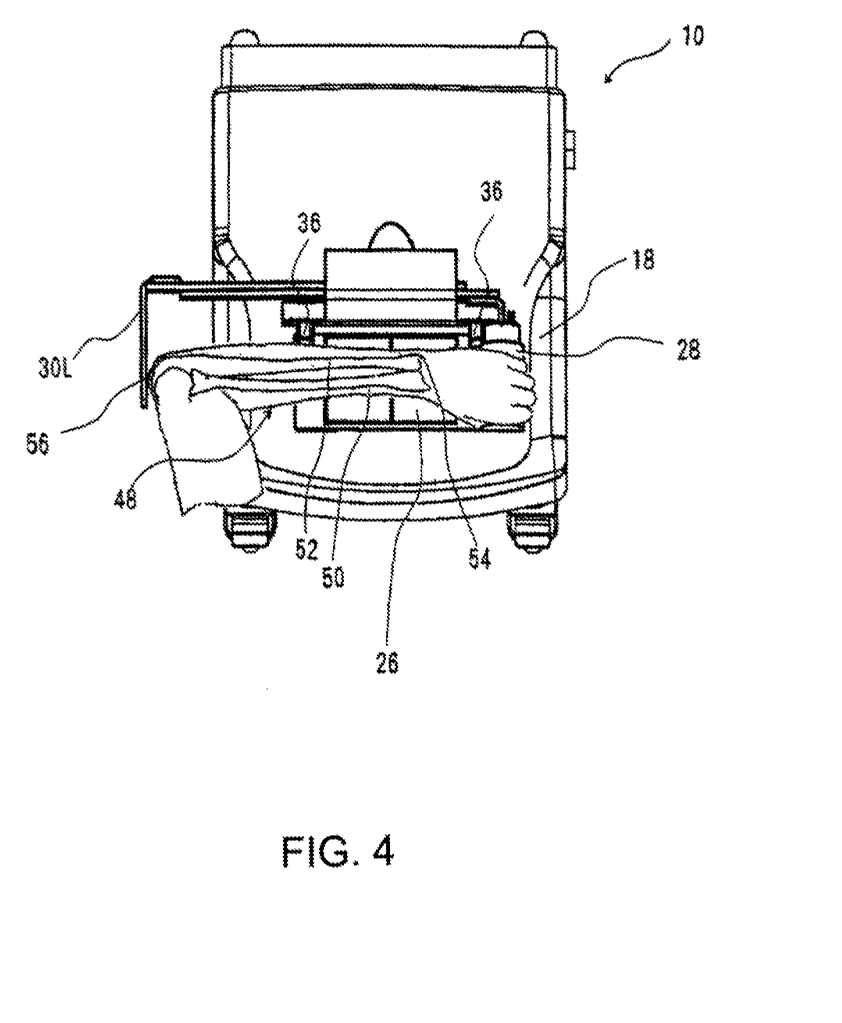
FIG. 4 is a plan view of the bone density measuring device according to the present embodiment, on which the left forearm is placed for measurement.

FIG. 4 illustrates the left forearm 48 being positioned on the table 18. Measurement of the bone density is performed in this state. The drawing also shows bones in the left forearm, for the purpose of explanation, of which a bone located toward the inward side of the arm; that the bone located on the lower side in FIG. 4, is a radius 50 and the other bone is an ulna 52. A process of the ulna 52 near the distal end is an ulna styloid process 54, and a portion at the proximal end of the ulna 52 is an olecranon 56.

When the examinee holds the grip 28 by the left hand and brings the left hand and the forearm contact with the two contact pad 36, the left forearm 48 positioned on the table 18. As illustrated, as the grip 28 is located on the right side of the top board 26, the distal end portions of the radius 50 and the ulna 52 are located on the top board 26, which is an X-ray irradiation range. Also, the elbow rest support rod 34L is moved in a sliding manner to bring the elbow rest 30L into contact with the olecranon 56. The position of the olecranon 56 is measured by detecting the amount of movement of the elbow rest support rod 34L. By capturing an X-ray image to specify the position of the ulna styloid process 54, the forearm length L can be calculated based on the specified position of the ulna styloid process 54 and the position of the elbow rest 30L. Alternatively, as the ulna styloid process 54 can be visually observed, the position of the ulna styloid process 54 can be specified by a method other than image processing of an X-ray image. For example, by disposing a laser marker generator moves in the right and left direction within the arm portion 22 and moving the laser marker generator to locate the laser marker at the position of the ulna styloid process 54, the position of the ulna styloid process 54 can be obtained from the position of the laser generator at this time.

When the right forearm is to be measured, the grip 28 is relocated to the left side of the rod support portion 32. When the grip 28 is positioned on the right side, the elbow rest 30R is inserted into and fixed within the grip 28. On removing the grip 28, the elbow rest 30R and the elbow rest support rod 34R are released and allowed to move in a sliding manner. When disposing the grip the left side, the elbow rest 30L is inserted into the grip 28. Thereafter, the measurement for the right forearm can be executed in a manner similar to that for the left forearm.

Figure 5:
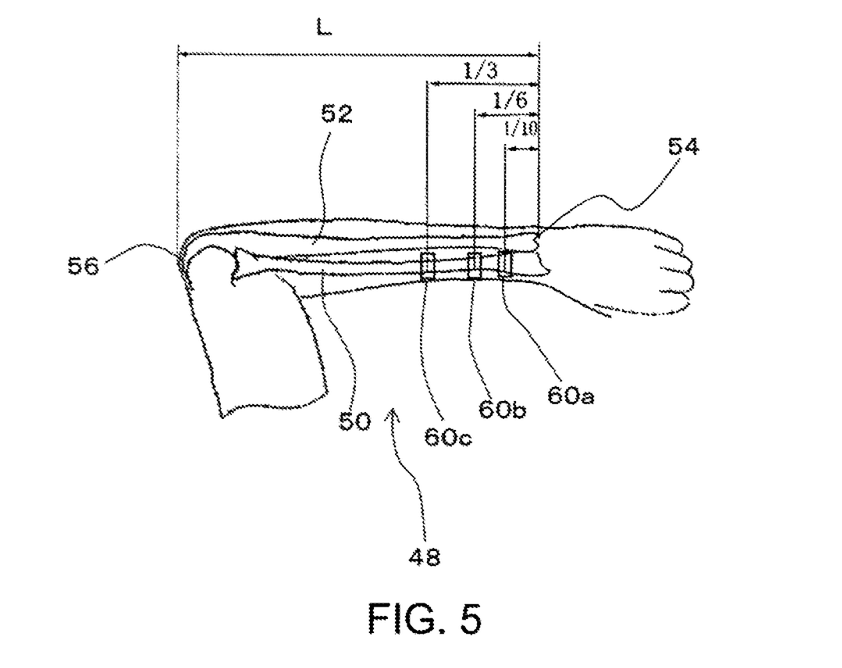
FIG. 5 is an explanatory view for explaining a region of interest with reference to the left forearm.

FIG. 5 illustrates example regions of interest 60a, 60b and 60c to be set in bone density measurement. As described above, the forearm length L is a length from the ulna styloid process 54 to the olecranon 56. The region of interest 60a set in a location spaced from the position of the ulna styloid process 54 by a length which is one-tenth (1/10) the forearm length L. Similarly, the regions of interest 60b and 60c are set at locations spaced from the position of the ulna styloid process 54 by lengths which are one-sixth (6/10) and one-third (1/3) the forearm length L, respectively. Hereinafter, each of the regions of interest 60a, 60b, and 60c will be referred to simply as the region of interest 60 unless these regions should be discriminated from each other.

Figure 6:
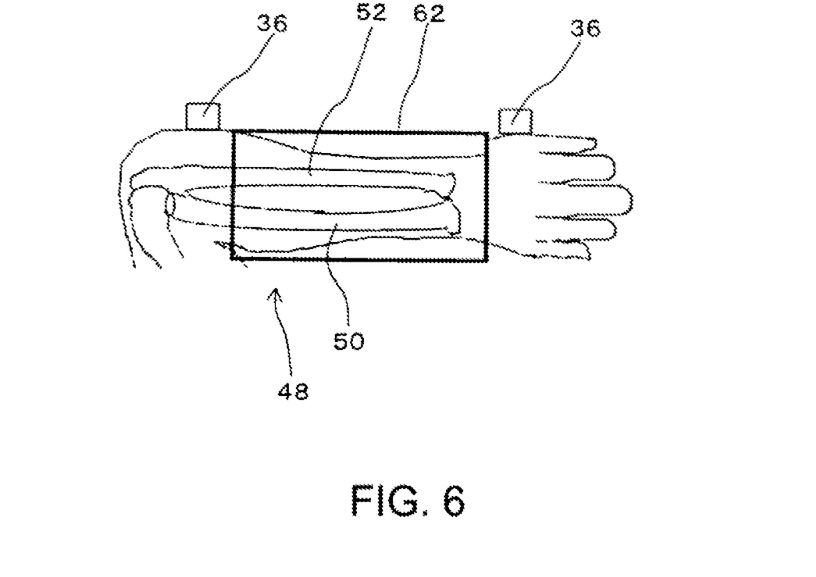
FIG. 6 is a diagram illustrating a relationship between a measurement region and the forearm.
Figure 7:
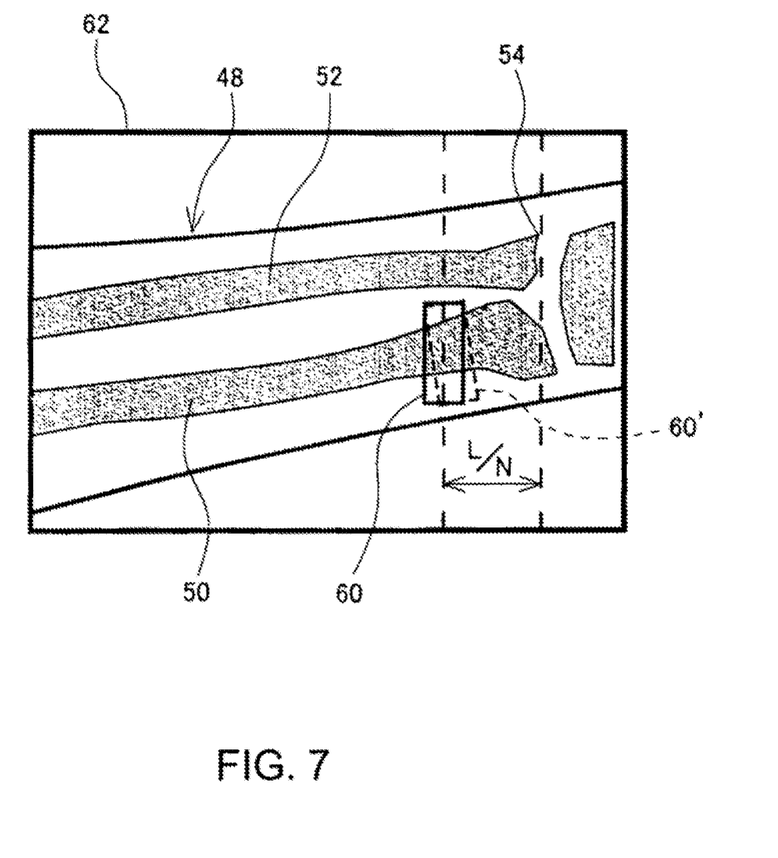
FIG. 7 is a diagram illustrating an example image captured with the left forearm being inclined.

FIG. 6 illustrates a relationship between the left forearm 48, particularly the radius 50 and the ulna 52, and a measurement region 62. The measurement region 62 corresponds to a range of which an X-ray image is to be captured. While concerning the following description, the drawings show the left forearm 48, the inclination of the forearm is common to the right forearm and the left forearm and therefore the forearm 48 will be simply described. Bringing the forearm 48 into close contact with the two contact pad 36 disposed toward the depth side of the table 18 makes the radius 50 and the ulna 52 extend substantially along the long side of the measurement region 62 having a rectangular shape. If the forearm 48 is not firmly in contact with the contact pads 36, the forearm 48 would be inclined with respect to the measurement region 62, as illustrated in FIG. 7, for example. In particular, with the bone density measuring device 10 as illustrated, the arm portion 22 is disposed above the table 18 so as to cover the table 18, which makes it difficult to confirm that the forearm 48 is in contact with the contact pads 36 located toward the depth portion of the table 18. There is therefore a possibility that measurement is performed without the forearm 48 being firmly in contact with the two contact pads 36.

FIG. 7 illustrates example image data which are captured with the forearm 48 being inclined. In conventional apparatuses, the long side and the short side of the measurement region 62 are respectively set in parallel to the orthogonal coordinate axes (X-axis and Y-axis). The region of interest 60 is defined based on these orthogonal coordinate axes. Accordingly, the distance to the region of interest 60 from the ulna styloid process 54 refers to the distance on the X-axis along the long side of the measurement region 62. Further, as illustrated, the region of interest 60 has a rectangular shape in which each side is parallel to any of the coordinate axes. The rectangle indicated by a dashed line in FIG. 7 is a region of interest 60' which is set with the forearm 48 being not inclined. It can be understood that inclination of the forearm 48 changes the position and inclination of the region of interest 60, which further causes displacement of the position of the bone included in the region of interest. As such, a change in the inclination of the forearm 48 changes a portion of the bone whose bone density is to be calculated, raising a problem that data comparison with high accuracy cannot be performed.

While the inclination of the forearm 48 can be mostly recognized from an X-ray image which is captured, abandoning these data and relocating the forearm 48 for further measurement would raise a problem of an increased amount of exposure to X-ray. It is therefore desired that even data obtained with the forearm 48 being inclined can be used.

Figure 8:
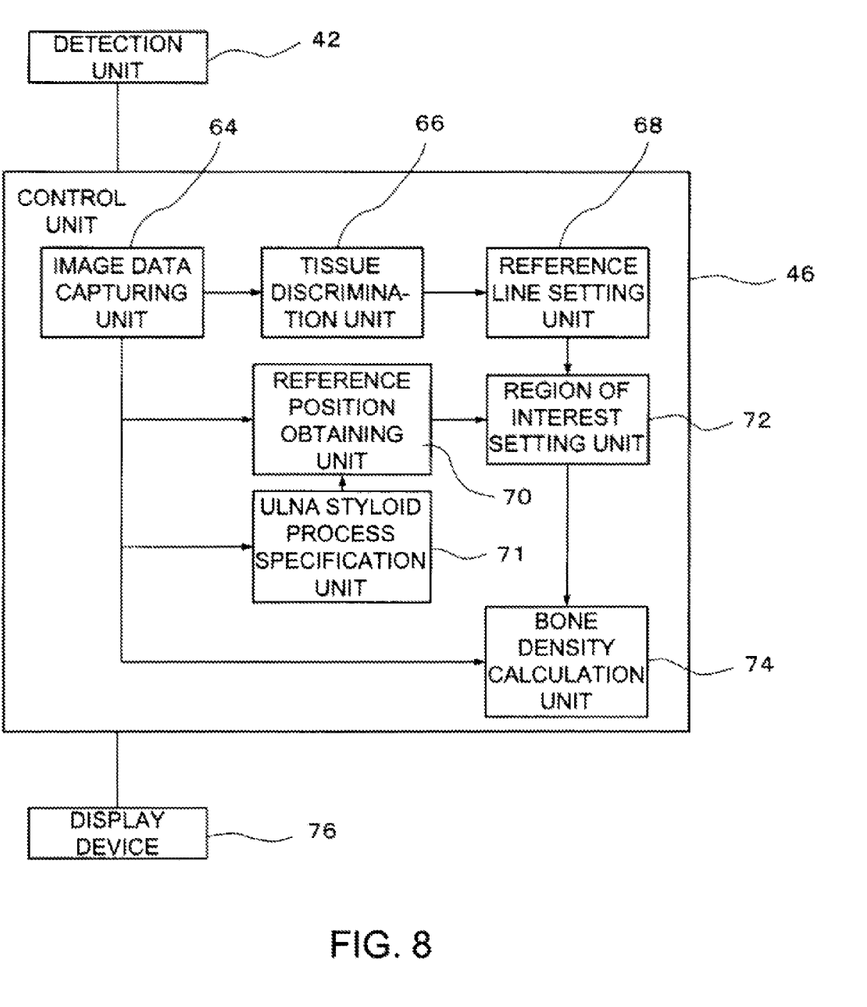
FIG. 8 is a block diagram illustrating functions of the bone density measuring device according to the present embodiment.

FIG. 8 is a block diagram showing functions of the bone density measuring device 10. The control unit 46 is operated in accordance with a predetermined program to thereby implement the function shown in each block. An image data capturing unit 64 forms image data based on a signal from the detection unit 42, so that the bone density measuring device 10 can obtain the image data. The image data are captured as illustrated in FIGS. 6 and 7, for example. A tissue discrimination unit 66 discriminates between an image portion corresponding to a bone and an image portion corresponding to a soft tissue within the image data which is captured. The tissue discrimination unit 66 discriminates between a bone portion and a soft tissue portion using a known method called energy subtraction, for example. A reference line setting unit 68 sets a reference line which is defined based on the forearm 48 using the image data which are discriminated, in order to cope with a case where the forearm 48 is placed on the table 18 in an inclined manner. Setting of the reference line will be described with reference to FIG. 9 through FIG. 11.

Figure 9:
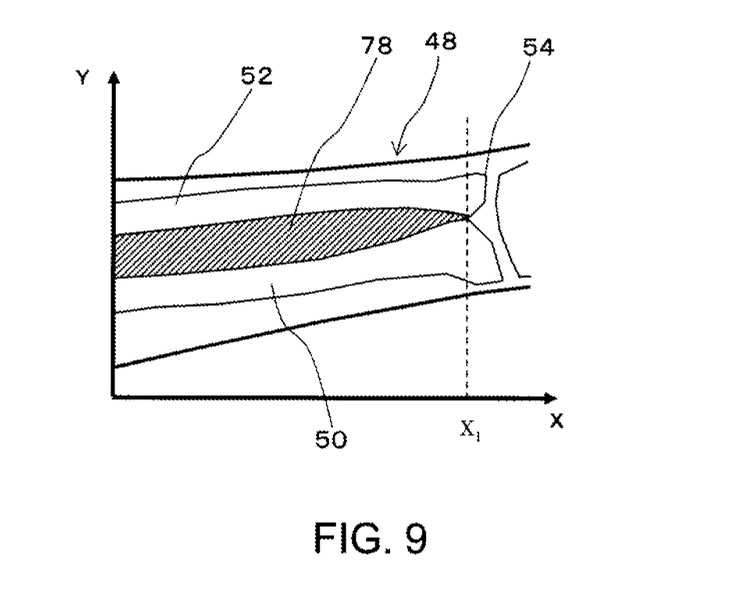
FIG. 9 is an explanatory view concerning acquisition of a reference line.
Figure 10:
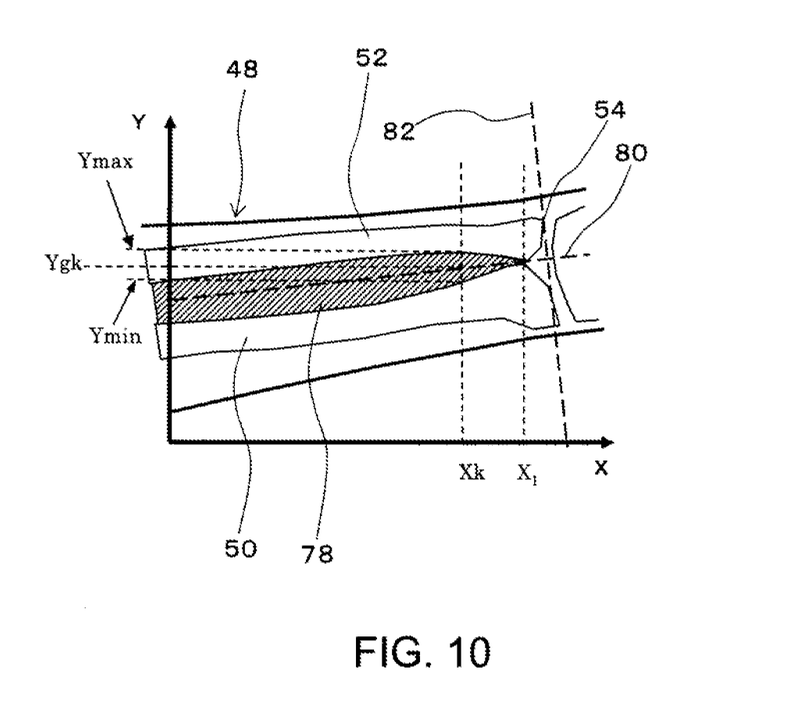
FIG. 10 is an explanatory view concerning acquisition of a reference line.

FIG. 9 illustrates an interosseous soft tissue 78 between the radius 50 and the ulna 52. The X-Y coordinate system which is shown is a system of coordinates fixed to the bone density measuring device 10, and the X-axis is defined in parallel to the horizontal side of the rectangular measurement region 62 illustrated in FIGS. 7 and 11, and the Y-axis is defined in parallel to the vertical side of the measurement region 62. The interval between the radius 50 and the ulna 52 extracted by the tissue discrimination unit 66 is narrowed at the distal end (the right side in FIG. 9). The position where the interval is narrowed is set as a coordinate X1. More specifically, with an X coordinate being moved toward the positive direction of the X-axis from the origin, the interval between the radius 50 and the ulna 52 is obtained, and the coordinate (X1) at which the interval is less than a predetermined value; e.g., 3 pixels, is set as a coordinate of an end of the interosseous soft tissue 78. Subsequently, as illustrated in FIG. 10, at a coordinate Xk located in the left direction from the coordinate X1, the maximum value Ymax and the minimum value Ymin of the Y coordinates of the interosseous soft tissue 78 are obtained. The mean value Ygk of the maximum value and the minimum value is then calculated.

$$Ygk=(Ymax+Ymin)/2$$

The mean value Ygk is a midpoint of the length of the interosseous soft tissue 78 in the Y-axis direction at the coordinate Xk. The midpoints Ygk are calculated concerning n coordinates Xk within a predetermined rants on the X-axis, and the linear approximation of the n midpoints Ygk which are obtained is obtained using the least squares method, for example. This approximate straight line is defined as a reference line 80, and the inclination of the reference line 80 with respect to the X-axis is defined as θ (see FIG. 11).

Figure 11:
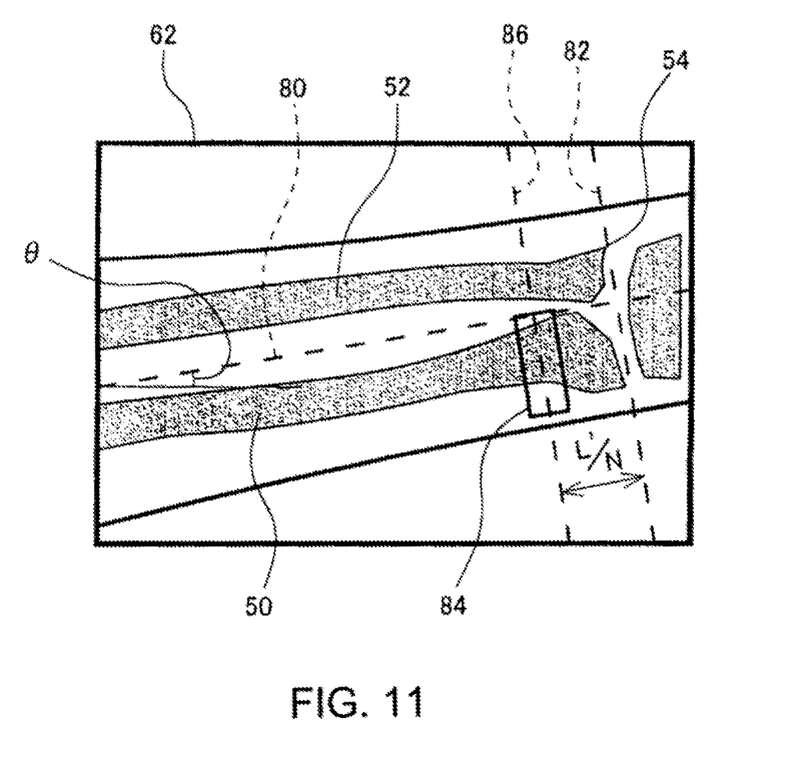
FIG. 11 is an explanatory view concerning setting of a reference position and setting of the region of interest.

A reference position obtaining unit 70 obtains the position of the ulna styloid process 54. As illustrated in FIG. 11, the position of the straight line passing the ulna styloid process 54 and orthogonal to the reference line 80 is set as a reference position 82. The ulna styloid process 54 can be specified using an ulna styloid process specification unit 71. Specifically, the ulna styloid process specification unit 71 defines an end of the bone portions located above the reference line 80 in the direction along the reference line 80 (in the case of FIG. 11, the right end) as the ulna styloid process 54. This can be achieved by processing the image data. Alternatively, in place of using the ulna styloid process specification unit 71, an operator of the bone density measuring device 10 may manually input the position of the ulna styloid process 54 to set the reference position. For example, the operator can locate a pointer at the ulna styloid process 54 on the image data which are displayed as illustrated in FIG. 11 and input the position of the ulna styloid process 54

(by clicking a mouse button, for example), thereby determining the reference position 82.

Then, a region of interest setting unit 72 sets a region of interest 84 based on the reference line 80 and the reference position 82. If the forearm 48 is inclined, the forearm length is also affected by the inclination. Accordingly, a corrected forearm length L' is obtained according to the following formula by correcting the forearm length L, measured using a sliding amount of the elbow rest 30L, in consideration of the inclination θ of the reference line 80.

$$L' = L/\cos\theta$$

The region of interest 84 is then set in a position spaced from the reference position 82 by a length of L'/N (N is a natural number) along the reference line 80. FIG. 11 illustrates the region of interest 84 in a position 86 at a distance corresponding to L'/10 from the reference position 82. The region of interest 84 has a rectangular shape and is disposed such that a short side of the rectangle is parallel to the reference line 80. The region of interest 84 is disposed to have the same width on both sides of the position 86. In the illustrated example, one short side is disposed on the reference line 80, and the region of interest 84 extends downwardly from the reference line 80. The lower end of the region of interest is set to a position a predetermined length spaced from the lower end of the radius in the position 86; e.g., 7 mm from the lower end of the radius along the straight line indicating the position 86. The width; that is, the length of the short side of the region of interest 84, can be set to 10 mm, for example. In other positions including L'/6, L'/3, and the like, the region of interest can be set in a similar manner.

A bone density calculation unit 74 calculates a bone density concerning the region of interest 84 which is set, using the image data which are captured. The calculated bone density is informed using a display device 76 or an external output apparatus such as a printing apparatus (not shown), for example.

As described above, in the bone density measuring device 10 according to the present embodiment, as the region of interest 84 is determined based on the reference line 80 fixed to the forearm 48, there can be prevented a displacement of a bone portion whose bone density is to be calculated caused by an inclination of the forearm 48 with respect to the coordinate axis fixed to the bone density measuring device 10. It is therefore possible to obtain values of the bone densities for substantially the same bone portion at a plurality of measurements which are performed at a certain interval. This structure enables more accurate recognition of a change in the bone density with time; e.g., the development of a symptom, the effect of a medicine, or the like, concerning one patient. Further, as the bone density can be measured at a predetermined measurement position not only in a plurality of measurements for observation for a change with time but also in a single measurement, reliability of data can be increased.

REFERENCE SIGN LIST

10 bone density measuring device, 18 table, 22 arm portion, 26 top board, 28 grip, 30L, 30R elbow rest, 34L, 34R elbow rest support rod, 46 control unit, 48 left forearm (forearm), 50 radius, 52 ulna, 54 ulna styloid process, 56 olecranon, 78 interosseous soft tissue, 80 reference line, 82 reference position, 84 region of interest.

The invention claimed is:

1. A bone density measuring device comprising:
    an image data capturing unit configured to capture an image including an ulna and a radius by X-ray photography;
    a tissue discrimination unit configured to discriminate between an image portion corresponding to a bone and an image portion corresponding to a soft tissue within image data which are captured;
    a reference line setting unit configured to obtain a direction in which an interosseous soft tissue between the ulna and the radius extends and set a reference line along the direction which is obtained;
    a reference position obtaining unit configured to obtain a reference position which is used as a reference for a measurement position;
    a region of interest setting unit configured to set at least one region of interest in a position at a predetermined distance from the reference position in a direction along the reference line; and
    a bone density calculation unit configured to calculate a bone density within the region of interest which is set;
    wherein the reference line setting unit obtains, in each of a plurality of positions on one coordinate axis of the image data which are captured, a midpoint of a length of the interosseous soft tissue in a direction orthogonal to the coordinate axis, and sets the reference line based on a plurality of midpoints which are obtained.

2. The bone density measuring device according to claim 1, wherein the region of interest which is to be set has a predetermined shape defined with reference to the reference line.

3. The bone density measuring device according to claim 1, wherein the reference line setting unit sets an approximate straight line of the plurality of midpoints which are obtained as the reference line.

4. The bone density measuring device according to claim 1, further comprising:
    an ulna styloid process specification unit configured to specify an ulna styloid process using the image portion corresponding to a bone which is discriminated,
    the reference position obtaining unit obtaining the reference position based on a position of the ulna styloid process.

5. The bone density measuring device according to claim 4, wherein the ulna styloid process specification unit determines a distal end of the image portion corresponding to a bone along the reference line on a predetermined side of the reference line as the ulna styloid process.

6. A method of measuring bone density using the bone density measuring device of claim 1, including the reference line setting unit obtaining a direction in which the interosseous soft tissue between the ulna and the radius extends and setting the reference line along the direction which is obtained, and
    including the reference line setting obtaining, in each of a plurality of positions on one coordinate axis of image data which are captured, a midpoint of a length of the interosseous soft tissue in a direction orthogonal to the coordinate axis, and setting the reference line based on a plurality of midpoints which are obtained.

* * * * *